US00PP15823P3

(12) United States Plant Patent
Murakami

(10) Patent No.: US PP15,823 P3
(45) Date of Patent: Jul. 5, 2005

(54) *PETUNIA* PLANT NAMED 'SUNBELKUPAPI'

(50) Latin Name: *Petunia hybrida*
Varietal Denomination: Sunbelkupapi

(75) Inventor: Yasuyuki Murakami, Gamo-gun (JP)

(73) Assignee: Suntory Flowers limited, Tokyo (JP)

( * ) Notice: Subject to any disclaimer, the term of this patent is extended or adjusted under 35 U.S.C. 154(b) by 73 days.

(21) Appl. No.: 10/723,818

(22) Filed: Nov. 25, 2003

(65) Prior Publication Data

US 2005/0114971 P1 May 26, 2005

(51) Int. Cl.[7] ..... A01H 5/00
(52) U.S. Cl. ..... Plt./356
(58) Field of Search ..... Plt./356

(56) References Cited

U.S. PATENT DOCUMENTS

PP10,278 P 3/1998 Murakami
PP10,279 P 3/1998 Murakami
PP10,287 P 3/1998 Murakami
PP10,355 P 4/1998 Murakami
PP13,715 P3 4/2003 Murakami

*Primary Examiner*—Bruce R. Campell
*Assistant Examiner*—S B McCormick-Ewoldt
(74) *Attorney, Agent, or Firm*—Christie, Parker and Hale, LLP

(57) ABSTRACT

Disclosed herein is a *Petunia* plant having decumbent growth habit. The *petunia* plant has abundant branching, particularly with respect to secondary branching, and great profusion of blooms with the entire of plant remaining of bloom for a considerable period of time. The flowers are single and very small with the petals having a deep purplish-pink color with a yellowish-white eye. The bottom color of corolla throat is brilliant yellow-green. The outside color of corolla throat is light greenish-yellow. The plant exhibits high resistance to rain, heat, drought and disease such as powdery mildew.

2 Drawing Sheets

Botanical/commercial classification: *Petunia hybrida*/*Petunia* Plant cv. 'Sunbelkupapi'.

BACKGROUND OF THE VARIETY

The *Petunia* is a very popular plant that is used for flower bedding and potting in the summer season. There are only a few small-flowered *Petunia* varieties, such as, 'Sunbelkuopi' (U.S. Plant Pat. No. 13,715), 'Sunbelkubu' (U.S. Plant Pat. No. 10,279), and 'Sunbelkuho' (U.S. Plant Pat. No. 10,278). These *Petunias* are of the decumbent type and have a very low plant height, abundant branching, and a high resistance to heat, rain and disease. Accordingly, this invention is aimed at obtaining a new *Petunia* variety having deep purplish-pink petal color with a yellowish-white eye, and very small flowers combined with the above features.

The new variety of *Petunia* plant according to this invention originated from the crossing with the *Petunia* variety named 'CBPS09' as the female parent, and the *Petunia* variety named 'CBPS04' as the male parent.

First of all, controlled crossings were conducted between the *Petunia* variety 'P49', as the female parent, and the *Petunia* variety 'CBP04', as male the parent, and the *Petunia* variety 'CBP04', as the female parent, and the *Petunia* variety 'P38', as the male parent, during March 1997 at Yokaichi-shi Shiga, Japan. In this connection, the *petunia* varieties 'P49', 'CBP04', 'P38', 'CBPS09' and 'CBPS04' are lines bred by us and are not filed in Japan or any other country. From each crossing 40 seedlings were obtained and the *Petunia* varieties 'CBPS09' and 'CBPS04' were selected from each crossing, in view of their decumbent type growth habit, abundant branching and flower color, at the end of December 1997. Then the controlled crossing between the *Petunia* variety 'CBPS09', as the female parent, and the

*Petunia* variety 'CBPS04', as the male parent, was conducted in 1998. From this crossing, 400 seedlings were obtained and 10 seedlings were selected, in October 1998, at Yokaichi-shi, Shiga, Japan. The 10 selected plants were propagated by cuttings and then grown in pots in both a greenhouse and in a field at Yokaichi-shi, Shiga, Japan from April to October 2000. The botanical characteristics of the selected plants were examined using the similar varieties 'Sunbelkupi' (U.S. Plant Pat. No. 10,287) and 'Sunbelochipi' (U.S. Plant Pat. No. 10,355) for comparison.

As a result, one plant was selected and it was concluded that the selected new *Petunia* variety is distinguishable from any other variety whose existence is known to us. The new variety was asexually reproduced using shoot cuttings and shown to be uniform and stable in its characteristics. This new variety of *Petunia* plant was named 'Sunbelkupapi'.

The new variety of the present invention can be readily distinguished from the 'Sunbelkupi' through an observation of the flower coloration. The new 'Sunbelkupapi' variety of the present invention forms deep purplish-pink flowers with a yellowish-white eye, the 'Sunbelkupi' variety forms vivid reddish-purple flowers.

In the following description, the color information is in accordance with The R.H.S. Colour Chart of The Royal Horticultural Society, London, England.

The main botanical characteristics of the comparison variety 'Sunbelkupi' are as follows:

Plant:

*Growth habit.*—Decumbent.

*Plant height.*—Approximately 6.0 cm.

*Spreading area of the plant.*—The stem expands to length of approximately 18 cm from the base.

*Blooming period.*—April to late October in the southern Kanto area, Japan. The plant shape does not change throughout this period.

Stem:

*Thickness.*—Approximately 1.2 mm.

*Pubescence.*—Normal to sparse.

*Branching.*—Abundant with a superior brunching.

*Length of internode.*—Approximately 1.3 cm.

Leaf:

*Shape.*—Lanceolate.

*Length.*—Approximately 3.5 cm.

*Width.*—Approximately 1.0 cm.

*Color.*—R.H.S. 137B(Dark green).

*Thickness.*—Approximately 0.2 mm.

*Pubescence.*—Sparse.

*Leaf attaching angle to stem.*—Slanted upward to horizontal.

Flower:

*Facing direction.*—Slanted upward to horizontal.

*Type.*—Single.

*Shape.*—Funnel-shaped, with five-fissures.

*Shape of petal tip.*—Rounded.

*Waving of petal.*—Weak.

*Lobation of petal.*—Shallow.

*Diameter.*—Approximately 2.8 cm.

*Color.*—Petal: R.H.S. 74A (Vivid reddish-purple).

*Bottom color of the corolla throat.*—R.H.S. 3A (Bright greenish-yellow).

*Outside color of corolla tube.*—R.H.S. 1D (Pale yellow-green) with R.H.S. 152B (Dark olive-green) lines.

*Reproductive organs.*—1 normal pistil and 5 normal stamens.

*Peduncle.*—Approximately0.7 mm in thickness, and Approximately 1.8 cm in length.

*Physiological and ecological characteristics.*—High resistance to heat, rain, drought and diseases such as Powdery mildew. The resistance to heat and rain is very strong.

COMPARISON TO PARENT VARIETIES 'CPBS09' AND 'CBPS04'

The petal color of the parent variety 'CBPS09' is R.H.S. N74A without eye, whereas that of 'Sunbelkupapi' is R.H.S. 73A with white grouped colored (R.H.S. 155C) eye, and the length of the leaf of 'CBS09' is shorter than that of 'Sunbelkupapi'.

The petal color of the parent variety 'CBPS04' is R.H.S. N74A with white group colored (R.H.S. 155C) eye and the length of the leaf of 'CBS04' is shorter than that of 'Sunbelkupapi'.

SUMMARY OF THE VARIETY

This new variety of *Petunia* plant 'Sunbelkupapi' has a decumbent growth habit with abundant branching, and forms single, very small deep purplish-pink flowers with a yellowish-white eye in a great profusion of blooms with the entire plant remaining in bloom for a considerable period of time. The plant has high tolerance to cold and heat, high resistance to diseases and rain.

BRIEF DESCRIPTION OF THE PHOTOGRAPHS

The depicted plants had been reproduced by cuttings and were photographed during June while growing outdoors in pots at an age of approximately six months at Yokaichi-shi, Shiga, Japan.

DESCRIPTION OF THE NEW VARIETY

Figure 1:
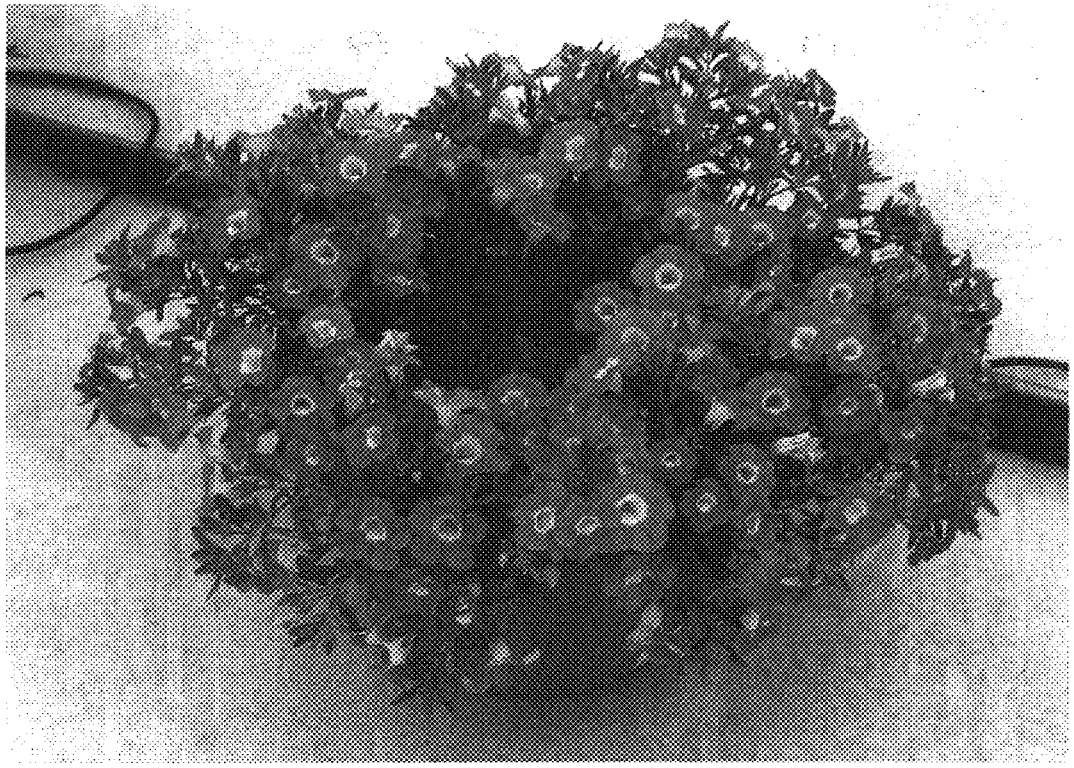
FIG. 1 is a photograph of flowers and leaves of the new variety of *Petunia* plant 'Sunbelkupapi'.
Figure 2:
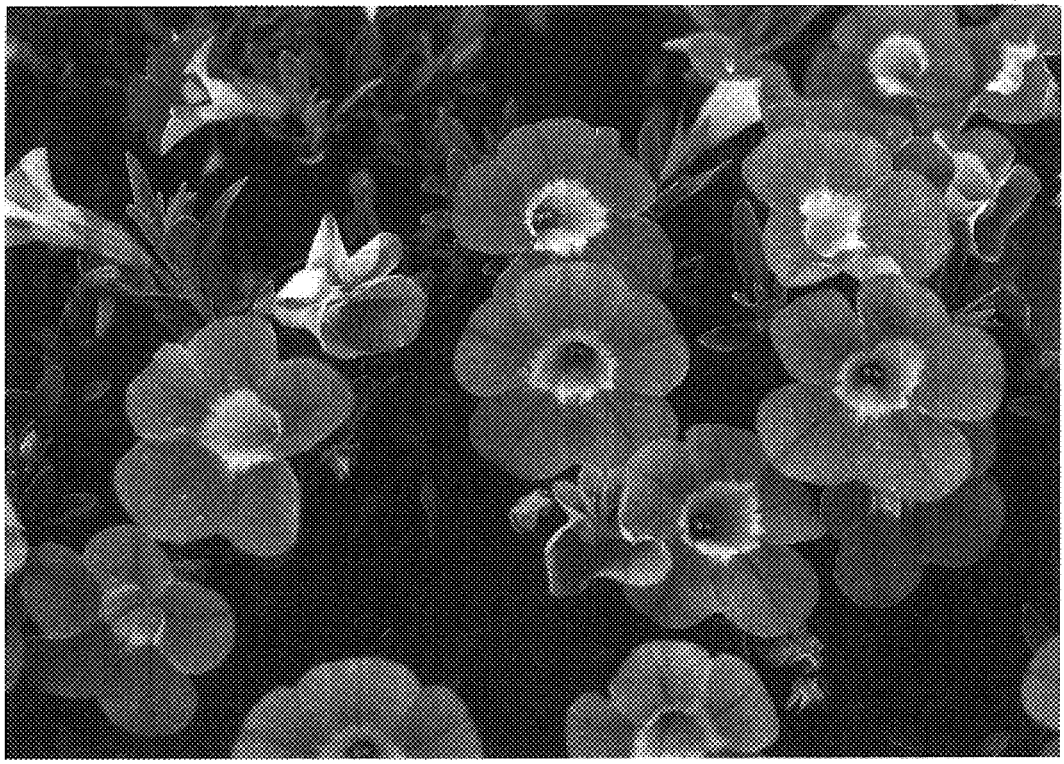
FIG. 2 is a photograph of flowers of the new variety of *Petunia* plant 'Sunbelkupapi'.

The botanical characteristics of the new and distinct variety of *Petunia* plant named 'Sunbelkupapi' are as follows were observed during June at Yokaichi-shi, Shiga, Japan:

Plant:

*Growth habit.*—Decumbent.

*Plant height.*—Approximately 6.5 cm.

*Spreading area of plant.*—The stem extends to length of approximately 30 cm from the base.

*Time to initiate root development.*—Approximately two weeks.

*Blooming period.*—April to late October in the southern Kanto area, Japan. The plant shape does not change throughout this period.

Stem:

*Color.*—Near R.H.S. 144B.

*Thickness.*—Approximately 2.0 mm.

*Pubescence.*—Sparse.

*Branching.*—Abundant with the superior branching propensity, especially secondary branches approximately 10 to 15 lateral branches.

*Length of internode.*—Approximately 1.5 cm.

Leaf:

*Whole shape.*—Lanceolate.

*Apex shape.*—Acute.

*Base shape.*—Attenuate.

*Length.*—Approximately 3.2 cm.

*Width.*—Approximately 1.1 cm.

*Color.*—Near R.H.S. 137A (Dark olive-green).

*Thickness.*—Approximately 0.3 mm.

*Pubescence.*—Sparse.

*Leaf attaching angle to stem.*—Slanted upward to horizontal.

*Margin.*—Entire.

*Venation.*—Central vein is conspicuous; lateral veins are not visible, color — Near R.H.S. 137C.

Flower:

*Facing direction.*—Slanted upward.

*Type.*—Single.

*Shape.*—Funnel-shaped, with five-fissures.

*Shape of petal tip.*—Rounded.

*Waving of petal.*—Weak.

*Petal texture.*—Smooth.

*Petal margin.*—Entire.

*Length of petal.*—Approximately 1 cm.

*Width of petal.*—Approximately 1.5 cm.

*Diameter.*—Approximately 3.2 cm.

*Bud color.*—Near R.H.S. 137B.

*Length of bud.*—Approximately 2.0 cm.

*Diameter of bud.*—Approximately 0.5 cm.

*Shape of bud.*—Lenticular.

*Color.*—Petal: Upper side near R.H.S. 73A (Deep purplish-pink), lower side near R.H.S. 155C; the eye color is near R.H.S. 155C (yellowish-white). Bottom color of corolla throat: near R.H.S. 7B (yellow group). Outside color of corolla tube: near R.H.S. 7D (yellow group).

*Length of corollar tube.*—Approximately 2.0 cm.

Sepals:

*Color.*—Near R.H.S. 137B.

*Length.*—Approximately 1.0 cm.

*Width.*—Approximately 0.3 cm.

*Reproductive organs.*—1 normal pistil and 5 normal stamens. The stigma is club-shaped and R.H.S.145A in coloration. The style is approximately 8 mm in length and R.H.S.145D in coloration. The ovary is R.H.S.145D in coloration. The stamens commonly are of variable length from approximately 5.0 to 8.0 mm. Pollen is formed in a quantity that is typical of *Petunia hybrida* and is near R.H.S.17A in coloration.

*Fertility.*—Fertile but self-incompatible.

*Peduncle.*—Approximately 0.9 mm in thickness, and approximately 1.5 cm in length. The texture is smooth.

*Seeds.*—R.H.S.N186A in coloration, approximately 0.6 mm in diameter, and generally round. The quantity is typical of *Petunia hybrida.*

*Physiological and ecological characteristics.*—High resistance to heat, rain, drought and diseases such as Powdery mildew. The resistance to heat and rain is very strong.

Blooming: A bloom commonly lasts approximately 10 days on the plant. Pinching is not necessary to ensure continuous blooming; however, it does tend to enhance bloom production.

This new variety of *Petunia* plant is most suitable for flower bedding and potting, particularly in hanging pots or in planters, and is excellent for use as a ground cover. Pinching of old blossoms will enhance the formation of new blossoms.

It is claimed:

1. A new and distinct *Petunia* plant, substantially as herein illustrated and described.

* * * * *